(12) United States Patent
Iaccino

(10) Patent No.: US 7,754,930 B2
(45) Date of Patent: Jul. 13, 2010

(54) USE OF ISOTOPIC ANALYSIS FOR DETERMINATION OF AROMATIC HYDROCARBONS PRODUCED FROM METHANE

(75) Inventor: Larry L. Iaccino, Seabrook, TX (US)

(73) Assignee: ExxonMobil Chemical Patents, Inc., Houston, TX (US)

( * ) Notice: Subject to any disclaimer, the term of this patent is extended or adjusted under 35 U.S.C. 154(b) by 325 days.

(21) Appl. No.: 11/805,868

(22) Filed: May 24, 2007

(65) Prior Publication Data

US 2007/0282145 A1 Dec. 6, 2007

Related U.S. Application Data

(60) Provisional application No. 60/810,095, filed on May 31, 2006.

(51) Int. Cl.
C07C 13/00 (2006.01)
(52) U.S. Cl. .......................................... 585/24; 585/941
(58) Field of Classification Search ................. 585/941, 585/24, 357, 269; 423/647.7, 644; 436/56, 436/57
See application file for complete search history.

(56) References Cited

U.S. PATENT DOCUMENTS

| | | | |
|---|---|---|---|
| 3,239,666 A * | 3/1966 | Newton et al. | 250/255 |
| 4,665,238 A * | 5/1987 | Imai et al. | 568/794 |
| 4,727,206 A | 2/1988 | Clayson et al. | |
| 5,026,937 A | 6/1991 | Bricker | |
| 5,336,825 A | 8/1994 | Choudhary et al. | |
| 5,348,982 A | 9/1994 | Herbolzheimer et al. | |
| 5,474,937 A * | 12/1995 | Anderson et al. | 436/27 |
| 5,491,270 A | 2/1996 | Chin et al. | |
| 5,936,135 A | 8/1999 | Choudhary et al. | |
| 6,114,279 A | 9/2000 | Fukui et al. | |
| 6,239,057 B1 | 5/2001 | Ichikawa et al. | |
| 6,426,442 B1 * | 7/2002 | Ichikawa et al. | 585/469 |
| 6,552,243 B2 | 4/2003 | Allison et al. | |
| 7,332,554 B2 | 2/2008 | Shaffer et al. | |
| 7,332,555 B2 | 2/2008 | Shaffer et al. | |
| 2002/0035305 A1 | 3/2002 | Ichikawa et al. | |
| 2003/0088133 A1* | 5/2003 | O'Rear | 585/323 |
| 2003/0144565 A1 | 7/2003 | Allison et al. | |
| 2004/0015025 A1 | 1/2004 | Bellussi et al. | |
| 2004/0097770 A1 | 5/2004 | Dakka et al. | |
| 2009/0017550 A1 | 1/2009 | Colle | |

FOREIGN PATENT DOCUMENTS

| | | |
|---|---|---|
| RU | 2 135 441 | 8/1999 |
| WO | 01/56957 | 8/2001 |
| WO | 2006/068800 | 6/2006 |
| WO | 2006/068814 | 6/2006 |
| WO | 2006/083409 | 8/2006 |

OTHER PUBLICATIONS

Catalytic conversion of Alkanes to Olefins by Carbon Dioxide Oxidative Dehydrogenation- A Review by Shaobin Wang and Z. H Zhu; Energy & Fuels (2004) 18, 1126-1139.*
Ma et al., "On the Induction Period of Methane Aromatization over Mo-Based Catalysts, Journal of Catalysis", 194, (2000), pp. 105-114.
Liu et al., "Non-oxidative Dehydroaromatization of Methane over Ga-promoted Mo-HZSM-5-based Catalysts", Applied Catalysis A: General, 214, (2001), pp. 95-102.
Japan Chemical Week Incorporating Asia Report, "Benzene Synthesized Directly from Methane: Mitsubishi Chem", The Chemical Daily Co., Ltd., vol. 46, No. 2337, ISSN 0047-1755, Oct. 6, 2005.
Wang et al., "Selective Dehydroaromatization of Methane toward Benzene on Re/HZSM-5 Catalysts and Effects of $CO/CO_2$ Addition", Journal of Catalysis, 190, 276-283 (2000).
Shu et al., "Pressurized Dehydrocondensation of Methane toward Benzene and Naphthalene on Mo/HZSM-5 Catalyst: Optimization of Reaction Parameters and Promotion by $CO_2$ Addition", Journal of Catalysis, 206, 134-142 (2002).
Jasper et al., "Process Patent Protection: Characterizing Synthetic Pathways by Stable-Isotopic Measurements", Pharmaceutical Technology, 2007, 31(3):68-73.
Ma et al., "Improvement of MTB reaction by addition of $CO_2$ $H_2$ and steam to methane feed on Mo/HZSM-5", Hokkaido University, Catalysis Research Center, Jul. 31, 2006.

* cited by examiner

Primary Examiner—Glenn A Caldarola
Assistant Examiner—Pamela Weiss
(74) Attorney, Agent, or Firm—Andrew B. Griffis

(57) ABSTRACT

Benzene and xylene are described having a unique distribution of deuterium and $^{13}C$ such that δ(deuterium) for each of the benzene and xylene is less than −250 and $δ(^{13}C)$ for the benzene is greater than −36 and for xylene is less than −24, wherein $$δ(deuterium)=(R'_{sample}/R'_{standard}-1)\times 1000$$

where $R'_{sample}$ is the ratio of deuterium to hydrogen in the benzene/xylene; and $R'_{standard}$ is the ratio of the natural abundance of deuterium to the natural abundance of hydrogen; and wherein $$δ(^{13}C)=(R''_{sample}/R''_{standard}-1)\times 1000$$

where $R''_{sample}$ is the ratio of $^{13}C$ to $^{12}C$ in the benzene/xylene; and $R''_{standard}$ is the ratio of the natural abundance of $^{13}C$ to the natural abundance of $^{12}C$.

59 Claims, No Drawings

USE OF ISOTOPIC ANALYSIS FOR DETERMINATION OF AROMATIC HYDROCARBONS PRODUCED FROM METHANE

CROSS REFERENCE TO RELATED APPLICATIONS

This application claims the benefit of Provisional Application Ser. No. 60/810,095 filed May 31, 2006, the disclosures of which are incorporated by reference in their entireties.

FIELD

This invention relates to the use of isotopic analysis for the determination of aromatic hydrocarbons produced from methane and, in particular, from natural gas.

BACKGROUND

Aromatic hydrocarbons, particularly benzene, toluene, ethylbenzene and xylenes, are important commodity chemicals in the petrochemical industry. Currently, aromatics are most frequently produced from petroleum-based feedstocks by a variety of processes, including catalytic reforming and catalytic cracking. However, as the world supplies of petroleum feedstocks decrease, there is a growing need to find alternative sources of aromatic hydrocarbons.

One possible alternative source of aromatic hydrocarbons is methane, which is the major constituent of natural gas. World reserves of natural gas are constantly being upgraded and more natural gas is currently being discovered than oil. Because of the problems associated with transportation of large volumes of natural gas, most of the natural gas produced along with oil, particularly at remote places, is flared and wasted. Hence the conversion of alkanes contained in natural gas directly to higher hydrocarbons, such as aromatics, is an attractive method of upgrading natural gas, providing the attendant technical difficulties can be overcome.

A large majority of the processes currently proposed for converting methane to liquid hydrocarbons involve initial conversion of the methane to synthesis gas, a blend of $H_2$ and CO. However, production of synthesis gas is capital and energy intensive and hence routes that do not require synthesis gas generation are preferred.

A number of alternative processes have been proposed for directly converting methane to higher hydrocarbons. One such process involves catalytic oxidative coupling of methane to olefins followed by the catalytic conversion of the olefins to liquid hydrocarbons, including aromatic hydrocarbons. For example, U.S. Pat. No. 5,336,825 discloses a two-step process for the oxidative conversion of methane to gasoline range hydrocarbons comprising aromatic hydrocarbons. In the first step, methane is converted to ethylene and minor amounts of $C_3$ and $C_4$ olefins in the presence of free oxygen using a rare earth metal promoted alkaline earth metal oxide catalyst at a temperature between 500° C. and 1000° C. The ethylene and higher olefins formed in the first step are then converted to gasoline range liquid hydrocarbons over an acidic solid catalyst containing a high silica pentasil zeolite.

However, oxidative coupling methods suffer from the problems that they involve highly exothermic and potentially hazardous methane combustion reactions and they generate large quantities of environmentally sensitive carbon oxides.

A potentially attractive route for upgrading methane directly into higher hydrocarbons, particularly ethylene, benzene and naphthalene, is dehydrocyclization or reductive coupling. This process typically involves contacting the methane with a catalyst comprising a metal, such as rhenium, tungsten or molybdenum, supported on a zeolite, such as ZSM-5, at high temperature, such as 600° C. to 1000° C. Frequently, the catalytically active species of the metal is the zero valent elemental form or a carbide or oxycarbide.

For example, U.S. Pat. No. 4,727,206 discloses a process for producing liquids rich in aromatic hydrocarbons by contacting methane at a temperature between 600° C. and 800° C. in the absence of oxygen with a catalyst composition comprising an aluminosilicate having a silica to alumina molar ratio of at least 5:1, said aluminosilicate being loaded with (i) gallium or a compound thereof and (ii) a metal or a compound thereof from Group VIIB of the Periodic Table.

In addition, U.S. Pat. No. 5,026,937 discloses a process for the aromatization of methane which comprises the steps of passing a feed stream, which comprises over 0.5 mole % hydrogen and 50 mole % methane, into a reaction zone having at least one bed of solid catalyst comprising ZSM-5, gallium and phosphorus-containing alumina at conversion conditions which include a temperature of 550° C. to 750° C., a pressure less than 10 atmospheres absolute (1000 kPaa) and a gas hourly space velocity of 400 to 7,500 $hr^{-1}$.

Moreover, U.S. Pat. No. 5,936,135 discloses a low temperature, non-oxidative process for the conversion of a lower alkane, such as methane or ethane, to aromatic hydrocarbons. In this process, the lower alkane is mixed with a higher olefin or paraffin, such as propylene or butene, and the mixture is contacted with a pretreated bifunctional pentasil zeolite catalyst, such as GaZSM-5, at a temperature of 300° C. to 600° C., a gas hourly space velocity of 1000 to 100000 $cm^3g^{-1}hr^{-1}$ and a pressure of 1 to 5 atmosphere (100 to 500 kPa). Pretreatment of the catalyst involves contacting the catalyst with a mixture of hydrogen and steam at a temperature 400° C. to 800° C., a pressure of 1 to 5 atmosphere (100 to 500 kPa) and a gas hourly space velocity of at least 500 $cm^3g^{-1}hr^{-1}$ for a period of at least 0.5 hour and then contacting the catalyst with air or oxygen at a temperature of 400° C. to 800° C., a gas hourly space velocity of at least 200 $cm^3g^{-1}hr^{-1}$ and a pressure of 1 to 5 atmosphere (100 to 500 kPa) for a period of at least 0.2 hour.

A particular difficulty in using natural gas as an aromatics source concerns the fact that many natural gas fields around the world contain large quantities, sometimes in excess of 50%, of carbon dioxide. Not only is carbon dioxide a target of increasing governmental regulation because of its potential contribution to global climate change, but also any process that requires separation and disposal of large quantities of carbon dioxide from natural gas is likely to be economically prohibitive. In fact, some natural gas fields have such high carbon dioxide levels as to be currently considered economically unrecoverable.

There is therefore a need for an improved process for converting methane to aromatic hydrocarbons, particularly where the methane is present in a natural gas stream containing large quantities of carbon dioxide.

U.S. Pat. Nos. 6,239,057 and 6,426,442 disclose a process for producing higher carbon number hydrocarbons, e.g., benzene, from low carbon number hydrocarbons, such as methane, by contacting the latter with a catalyst comprising a porous support, such as ZSM-5, which has dispersed thereon rhenium and a promoter metal such as iron, cobalt, vanadium, manganese, molybdenum, tungsten or a mixture thereof. After impregnation of the support with the rhenium and promoter metal, the catalyst is activated by treatment with hydrogen and/or methane at a temperature of about 100° C. to about 800° C. for a time of about 0.5 hr. to about 100 hr. The addition of CO or $CO_2$ to the feed is said to increase the selectivity to benzene and the stability of the catalyst. The ratio CO and/or $CO_2$ to methane can vary from about 0.001 to about 0.5 and preferably from about 0.01 to about 0.3.

Russian Patent No. 2,135,441 discloses a process for converting methane to heavier hydrocarbons, in which the methane is mixed with at least 5 wt % of a $C_3$+ hydrocarbon, such as benzene, and then contacted in a multi-stage reactor system with a catalyst comprising metallic platinum having a degree of oxidation greater than zero at a methane partial pressure of at least 0.05 MPa and a temperature of at least 440° C. Hydrogen generated in the process may be contacted with oxides of carbon to generate additional methane that, after removal of the co-produced water, can be added to the methane feed. The products of the methane conversion are a $C_2$-$C_4$ gaseous phase and a $C_5$+ liquid phase but, according the Examples, there is little (less than 5 wt %) or no net increase in aromatic rings as compared with the feed.

In our co-pending U.S. Patent Application Ser. No. 60/638,922, filed on Dec. 22, 2004, the entire contents of which are incorporated herein by reference, we have described a process for converting methane to higher hydrocarbons including aromatic hydrocarbons, the process comprising (a) contacting a feed containing methane with a dehydrocyclization catalyst under conditions effective to convert the methane to aromatic hydrocarbons and produce a first effluent stream comprising aromatic hydrocarbons and hydrogen, wherein the first effluent stream comprises at least 5 wt % more aromatic rings than said feed; and (b) reacting at least part of the hydrogen from the first effluent stream with an oxygen-containing species, particularly CO and/or $CO_2$, to produce a second effluent stream having a reduced hydrogen content compared with the first effluent stream.

Further, in our co-pending U.S. Patent Application Ser. No. 60/638,605, filed Dec. 22, 2004, the entire contents of which are incorporated herein by reference, we have described a process for converting methane to alkylated aromatic hydrocarbons, the process comprising contacting a feed containing methane with a dehydrocyclization catalyst under conditions effective to convert said methane to aromatic hydrocarbons and produce a first effluent stream comprising aromatic hydrocarbons and hydrogen; and contacting at least a portion of said aromatic hydrocarbon from said first effluent stream with an alkylating agent under conditions effective to alkylate said aromatic hydrocarbon and produce an alkylated aromatic hydrocarbon having more alkyl side chains than said aromatic hydrocarbon prior to the alkylating.

Aromatic hydrocarbons, like all hydrocarbons, inherently contain deuterium and $^{13}C$ in amounts that can vary according to the source of the carbon and hydrogen atoms in the molecule. Moreover, studies of isotope distributions have shown that the amounts of deuterium and $^{13}C$ in naturally-occurring geologic methane are significantly different from the amounts of deuterium and $^{13}C$ in naphtha and that the amount of $^{13}C$ in naturally-occurring geologic $CO_2$ is significantly different from the amounts of $^{13}C$ in naturally-occurring geologic methane and in naphtha. Thus the present invention is based on the realization that the amounts of deuterium and $^{13}C$ present in an aromatic hydrocarbon product can serve to differentiate between an aromatic hydrocarbon produced from naphtha, the same aromatic hydrocarbon produced by dehydrocyclization of naturally-occurring geologic methane alone and the same aromatic hydrocarbon produced by dehydrocyclization of naturally-occurring geologic methane and methane produced from $CO_2$.

SUMMARY

For the purposes of this invention the measure of isotope abundance for deuterium in a benzene or xylene sample is defined as:

$$\delta(\text{deuterium})=(R'_{sample}/R'_{standard}-1)\times 1000$$

where $R'_{sample}$ is the ratio of deuterium to hydrogen in the benzene or xylene; and $R'_{standard}$ is the ratio of the natural abundance of deuterium to the natural abundance of hydrogen (which is equal to 0.00015/0.99985); and and the measure of isotope abundance for $^{13}C$ in the sample is defined as:

$$\delta(^{13}C)=(R''_{sample}/R''_{standard}-1)\times 1000$$

where $R''_{sample}$ is the ratio of $^{13}C$ to $^{12}C$ in the benzene or xylene; and $R''_{standard}$ is the ratio of the natural abundance of $^{13}C$ to the natural abundance of $^{12}C$ (which is equal to 0.01109/0.98891).

In one aspect, the present invention resides in benzene comprising deuterium and $^{13}C$ in amounts such that $\delta(\text{deuterium})$ for the benzene is less than −250 and $\delta(^{13}C)$ for the benzene is greater than −36 wherein $\delta(\text{deuterium})$ and $\delta(^{13}C)$ are as defined in the preceding paragraph.

Preferably, the $\delta(\text{deuterium})$ for the benzene is greater than −450 and less than −250 and the $\delta(^{13}C)$ for the benzene is greater than −36 and less than −24.

In another aspect, the present invention resides in benzene, comprising deuterium and $^{13}C$ in amounts such that the $\delta(\text{deuterium})$ value is less than −250 or the $\delta(^{13}C)$ value is less than −24, the benzene being produced by a process comprising:
  (a) contacting a feed containing methane with a dehydrocyclization catalyst under conditions effective to convert the methane to aromatic hydrocarbons including benzene and produce a first effluent stream comprising aromatic hydrocarbons and hydrogen, wherein the first effluent stream comprises at least 5 wt % more aromatic rings than said feed;
  (b) reacting at least part of the hydrogen from the first effluent stream with CO and/or $CO_2$, to produce a second effluent stream having a reduced hydrogen content and an enhanced hydrocarbon content as compared with the first effluent stream; and
  (c) recycling at least part of the second effluent stream to said contacting (a).

In yet another aspect, the present invention resides in xylene comprising deuterium and $^{13}C$ in amounts such that the $\delta(\text{deuterium})$ value for the xylene is less than −250 and the $\delta(^{13}C)$ value for the xylene is less than −24.

In a further aspect, the present invention resides in xylene comprising deuterium and $^{13}C$ in amounts such that the $\delta(\text{deuterium})$ value for the xylene is less than −250 or the $\delta(^{13}C)$ value for the xylene is less than −32.

In still yet a further aspect, the present invention resides in xylene comprising deuterium and $^{13}C$ in amounts such that the $\delta(\text{deuterium})$ value is less than −250 or the $\delta(^{13}C)$ value is less than −24, the xylene being produced by a process comprising:
  (a) contacting a feed containing methane with a dehydrocyclization catalyst under conditions effective to convert the methane to aromatic hydrocarbons including benzene and produce a first effluent stream comprising aromatic hydrocarbons and hydrogen; and (b) contacting at least a portion of the benzene from said first effluent stream with an alkylating agent under conditions effective to alkylate said benzene and produce alkylbenzene.

In an additional aspect, the present invention resides in xylene comprising deuterium and $^{13}C$ in amounts such that the $\delta$(deuterium) value is less than −250 or the $\delta(^{13}C)$ value is less than −24, the xylene being produced by a process comprising:

(a) contacting a feed containing methane with a dehydrocyclization catalyst under conditions effective to convert the methane to aromatic hydrocarbons including benzene and produce a first effluent stream comprising aromatic hydrocarbons and hydrogen;

(b) reacting at least part of the hydrogen from the first effluent stream with CO and/or $CO_2$, to produce a second effluent stream having a reduced hydrogen content and an enhanced hydrocarbon content as compared with the first effluent stream;

(c) recycling at least part of the second effluent stream to said contacting (a); and (d) contacting at least a portion of the benzene from said first effluent stream with an alkylating agent under conditions effective to alkylate said benzene and produce alkylbenzene.

In yet an additional aspect, the present invention resides in the use of measured amounts of deuterium and $^{13}C$ present in an aromatic hydrocarbon product as a means to identify the type of feedstock and/or production process used in its manufacture.

DETAILED DESCRIPTION OF THE EMBODIMENTS

Described herein are benzene and xylene, together with the derivatives thereof, wherein the benzene and xylene have a novel distribution of the isotopes deuterium and $^{13}C$ by virtue of their production by a process involving the dehydrocyclization of methane. As will be discussed in more detail below, in the case of benzene the process further involves reacting at least part of the hydrogen byproduct of the dehydrocyclization step with CO and/or $CO_2$, preferably coproduced with the methane from the same natural gas stream, to produce additional hydrocarbons which are recycled to the dehydrocyclization step. In the case of xylene, the process further involves contacting at least a portion of the benzene from the dehydrocyclization step with a alkylating agent, preferably a mixture or reaction product of the hydrogen byproduct of the dehydrocyclization step and CO and/or $CO_2$ coproduced with the methane. Depending on the alkylating agent employed, the alkylbenzene produced in the alkylation step can be one or more xylenes or can be converted to xylenes by processes well known in the art, such as isomerization, transalkylation, and disproportionation.

Also described herein is a method of using the measured amounts of deuterium and $^{13}C$ present in an aromatic hydrocarbon product as a means to identify the type of feedstock and production process used in its manufacture. Specifically the amounts of deuterium and $^{13}C$ can serve to differentiate between an aromatic hydrocarbon produced from naphtha, the same aromatic hydrocarbon produced by dehydrocyclization of naturally-occurring geologic methane alone and the same aromatic hydrocarbon produced by dehydrocyclization of naturally-occurring geologic methane and methane and/or methanol produced from $CO_2$.

Feedstock

Any methane-containing feedstock can be used to produce the benzene and xylene of the invention but in general the present process is intended for use with a natural gas feedstock. Methane-containing feedstocks, such as natural gas, typically contain carbon dioxide and ethane in addition to methane. Ethane and other aliphatic hydrocarbons that may be present in the feed can of course be converted to desired aromatics products in the dehydrocyclization step. In addition, as will be discussed below, carbon dioxide can also be converted to useful aromatics products either directly in the dehydrocyclization step or indirectly through conversion to hydrocarbons in the hydrogen rejection step or through alkylation of the aromatics produced in the dehydrocyclization step.

Nitrogen and/or sulfur impurities are also typically present in methane-containing streams and may be removed, or reduced to low levels, prior to use of the streams in the process of the invention. In an embodiment, the feed to the dehydrocyclization step contains less than 100 ppm, for example less than 10 ppm, such as less than 1 ppm each of nitrogen and sulfur compounds.

In addition to methane, the feed to the dehydrocyclization step may contain at least one of hydrogen, water, carbon monoxide and carbon dioxide in order to assist in coke mitigation. These additives can be introduced as separate co-feeds or can be present in the methane stream, such as, for example, where the methane stream is derived from natural gas containing carbon dioxide. Other sources of carbon dioxide may include flue gases, LNG plants, hydrogen plants, ammonia plants, glycol plants and phthalic anhydride plants.

In one embodiment, the feed to the dehydrocyclization step contains carbon dioxide and comprises about 90 to about 99.9 mol %, such as about 97 to about 99 mol %, methane and about 0.1 to about 10 mol %, such as about 1 to about 3 mol %, $CO_2$. In another embodiment, the feed to the dehydrocyclization step contains carbon monoxide and comprises about 80 to about 99.9 mol %, such as about 94 to about 99 mol %, methane and about 0.1 to about 20 mol %, such as about 1 to about 6 mol %, CO. In a further embodiment, the feed to the dehydrocyclization step contains steam and comprises about 90 to about 99.9 mol %, such as about 97 to about 99 mol %, methane and about 0.1 to about 10 mol %, such as about 1 to about 5 mol %, steam. In yet a further embodiment, the feed to the dehydrocyclization step contains hydrogen and comprises about 80 to about 99.9 mol %, such as about 95 to about 99 mol %, methane and about 0.1 to about 20 mol %, such as about 1 to about 5 mol %, hydrogen.

The feed to the dehydrocyclization step can also contain higher hydrocarbons than methane, including aromatic hydrocarbons. Such higher hydrocarbons can be recycled from the hydrogen rejection step, added as separate co-feeds or can be present in the methane stream, such as, for example, when ethane is present in a natural gas feed. Higher hydrocarbons recycled from the hydrogen rejection step typically include one-ring aromatics and/or paraffins and olefins having predominately 6 or less, such as 5 or less, for example 4 or less, typically 3 or less carbon atoms. In general, the feed to the dehydrocyclization step contains less than 5 wt %, such as less than 3 wt %, of $C_3$+ hydrocarbons.

Dehydrocyclization

In the dehydrocyclization step of the present process, the methane containing feedstock is contacted with a dehydrocyclization catalyst under conditions, normally non-oxidizing conditions and preferably reducing conditions, effective to convert the methane to higher hydrocarbons, including benzene and naphthalene. The principal net reactions involved are as follows:

$$2CH_4 \leftrightarrows C_2H_4 + 2H_2 \quad \text{(Reaction 1)}$$

$$6CH_4 \leftrightarrows C_6H_6 + 9H_2 \quad \text{(Reaction 2)}$$

$$10CH_4 \leftrightarrows C_{10}H_8 + 16H_2 \quad \text{(Reaction 3)}$$

Carbon monoxide and/or dioxide that may be present in the feed improves catalyst activity and stability by facilitating reactions such as:

$$CO_2 + coke \rightarrow 2CO \quad \text{(Reaction 4)}$$

but negatively impacts equilibrium by allowing competing net reactions, such as;

$$CO_2 + CH_4 \leftrightarrows 2CO + 2H_2 \quad \text{(Reaction 5)}.$$

Suitable conditions for the dehydrocyclization step include a temperature of about 400° C. to about 1200° C., such as about 500° C. to about 975° C., for example about 600° C. to about 950° C., a pressure of about 1 kPa to about 1000 kPa, such as about 10 to about 500 kPa, for example about 50 kPa to about 200 kPa and a weight hourly space velocity of about 0.01 to about 1000 hr$^{-1}$, such as about 0.1 to about 500 hr$^{-1}$, for example about 1 to about 20 hr$^{-1}$. Conveniently, the dehydrocyclization step is conducted in the absence of $O_2$.

Any dehydrocyclization catalyst effective to convert methane to aromatics can be used in the present process, although generally the catalyst will include a metal component, particularly a transition metal or compound thereof, on an inorganic support. Conveniently, the metal component is present in an amount between about 0.1% and about 20%, such as between about 1% and about 10%, by weight of the total catalyst. Generally, the metal will be present in the catalyst in elemental form or as a carbide species.

Suitable metal components for the catalyst include calcium, magnesium, barium, yttrium, lanthanum, scandium, cerium, titanium, zirconium, hafnium, vanadium, niobium, tantalum, chromium, molybdenum, tungsten, manganese, rhenium, iron, ruthenium, cobalt, rhodium, iridium, nickel, palladium, copper, silver, gold, zinc, aluminum, gallium, silicon, germanium, indium, tin, lead, bismuth and transuranium metals. Such metal components may be present in elemental form or as metal compounds, such as oxides, carbides, nitrides and/or phosphides, and may be employed alone or in combination. Platinum and osmium can also be used as one of the metal component but, in general, are not preferred.

The inorganic support may be either amorphous or crystalline and in particular may be an oxide, carbide or nitride of boron, aluminum, silicon, phosphorous, titanium, scandium, chromium, vanadium, magnesium, manganese, iron, zinc, gallium, germanium, yttrium, zirconium, niobium, molybdenum, indium, tin, barium, lanthanum, hafnium, cerium, tantalum, tungsten, or other transuranium elements. In addition, the support may be a porous material, such as a microporous crystalline material or a mesoporous material. As used herein the term "microporous" refers to pores having a diameter of less than 2 nanometers, whereas the term "mesoporous" refers to pores having a diameter of from 2 to 50 nanometers.

Suitable microporous crystalline materials include silicates, aluminosilicates, titanosilicates, aluminophosphates, metallophosphates, silicoaluminophosphates or their mixtures. Such microporous crystalline materials include materials having the framework types MFI (e.g., ZSM-5 and silicalite), MEL (e.g., ZSM-11), MTW (e.g., ZSM-12), TON (e.g., ZSM-22), MTT (e.g., ZSM-23), FER (e.g., ZSM-35), MFS (e.g., ZSM-57), MWW (e.g., MCM-22, PSH-3, SSZ-25, ERB-1, ITQ-1, ITQ-2, MCM-36, MCM-49 and MCM-56), IWR (e.g., ITQ-24), KFI (e.g., ZK-5), BEA (e.g., zeolite beta), ITH (e.g., ITQ-13), MOR (e.g., mordenite), FAU (e.g., zeolites X, Y, ultrastabilized Y and dealuminized Y), LTL (e.g., zeolite L), IWw (e.g., ITQ-22), VFI (e.g., VPI-5), AEL (e.g., SAPO-11), AFI (e.g., ALPO-5) and AFO (SAPO-41), as well as materials such as MCM-68, EMM-1, EMM-2, ITQ-23, ITQ-24, ITQ-25, ITQ-26, ETS-2, ETS-10, SAPO-17, SAPO-34 and SAPO-35. Suitable mesoporous materials include MCM-41, MCM-48, MCM-50, FSM-16 and SBA-15.

Examples of preferred catalysts include molybdenum, tungsten, zinc, rhenium and compounds and combinations thereof on ZSM-5, silica or alumina.

The metal component can be dispersed on the inorganic support by any means well known in the art such as co-precipitation, incipient wetness, evaporation, impregnation, spray-drying, sol-gel, ion-exchange, chemical vapor deposition, diffusion and physical mixing. In addition, the inorganic support can be modified by known methods, such as, for example, steaming, acid washing, caustic washing and/or treatment with silicon-containing compounds, phosphorus-containing compounds, and/or elements or compounds of Groups 1, 2, 3 and 13 of the Periodic Table of Elements. Such modifications can be used to alter the surface activity of the support and hinder or enhance access to any internal pore structure of the support.

The dehydrocyclization step is conducted by contacting the methane-containing feedstock with the dehydrocyclization catalyst in one or more fixed bed, moving bed or fluidized bed reaction zones. Generally, the feedstock is contacted in the or each reaction zone with a moving bed of dehydrocyclization catalyst, wherein the feedstock flows countercurrent to the direction of movement of the dehydrocyclization catalyst. In one embodiment, the reaction zone comprises a settling bed reactor, by which is meant a vertically disposed reactor in which particulate catalyst enters at or near the top of the reactor and flows under gravity to form a catalyst bed, while the feed enters the reactor at or near the base of the reactor and flows upwardly through the catalyst bed. In an alternative embodiment, the reaction zone comprises a plurality of series-connected fluidized bed reactors in which particulate catalyst is cascaded in one direction from one reactor to the next adjacent reactor in the series, while the feed is passed through and between the reactors in the opposite direction.

The major components of the effluent from the dehydrocyclization step are hydrogen, benzene, naphthalene, carbon monoxide, ethylene, and unreacted methane. Typically, the effluent contains at least 5 wt %, such as at least 10 wt %, for example at least 20 wt %, preferably at least 30 wt %, more aromatic rings than the feed. This means that the total number of aromatic rings in the dehydrocyclization effluent stream will normally exceed the total number of aromatic rings in the feed by at least 5 wt %. For example, if the feed contains 1 wt % of aromatic rings, the dehydrocyclization effluent stream will contain at least 6 wt % of aromatic rings. Changes in substituents on any aromatic rings between the feed and the first effluent stream are not included in this calculation.

In one embodiment of the invention, the benzene is recovered from the dehydrocyclization effluent, for example, by solvent extraction followed by fractionation. However, as will be discussed below, at least part of the benzene can be subjected to an alkylation step, before or after product recovery, to produce higher value materials, such as xylenes.

Hydrogen Management

Since hydrogen is a major component of the dehydrocyclization effluent, after recovery of the aromatic products, the effluent can be subjected to a hydrogen rejection step to convert at least part of hydrogen to additional hydrocarbons, which can then be recycled with the unreacted methane to the dehydrocyclization step to maximize feed utilization. Typically the hydrogen rejection step comprises reacting at least part of the hydrogen in the dehydrocyclization effluent with CO and/or $CO_2$, preferably coproduced with the feed methane from a natural gas stream.

Conveniently, the hydrogen rejection step includes (i) methanation and/or ethanation, (ii) a Fischer-Tropsch process, (iii) synthesis of $C_1$ to $C_3$ alcohols, particularly methanol, and other oxygenates, and/or (iv) synthesis of light olefins, paraffins and/or aromatics by way of a methanol or dimethyl ether intermediate. These steps may be employed sequentially to gain the greatest benefit; for example Fischer-Tropsch may first be employed to yield a $C_2$+ enriched stream followed by methanation to achieve high conversion of the $H_2$.

Typically, as described below, the hydrogen rejection step will generate paraffins and olefins, in which case, after separation of the co-produced water, the portion recycled to the dehydrocyclization step conveniently comprises, paraffins or olefins with 6 or less carbon atoms, such as 5 or less carbon atoms, for example 4 or less carbon atoms or 3 or less carbon atoms. Where, the hydrocarbons produced in the hydrogen rejection step comprise aromatics, the portion recycled to the dehydrocyclization step conveniently comprises single ring aromatic species.

Methanation/Ethanation

In one embodiment the hydrogen rejection step comprises reaction of at least part of the hydrogen in the dehydrocyclization effluent with carbon dioxide to produce methane and/or ethane according to the following net reactions:

$$CO_2 + 4H_2 \leftrightarrows CH_4 + 2H_2O \quad \text{(Reaction 6)}$$

$$2CO_2 + 7H_2 \leftrightarrows C_2H_6 + 4H_2O \quad \text{(Reaction 7)}$$

The carbon dioxide employed is conveniently part of a natural gas stream and preferably the same natural gas stream used as the feed to the dehydrocyclization step. Where the carbon dioxide is part of a methane-containing stream, the $CO_2$:$CH_4$ of the stream is conveniently maintained between about 1:1 and about 0.1:1. Mixing of the carbon dioxide-containing stream and the dehydrocyclization effluent is conveniently achieved by supplying the gaseous feeds to the inlet of a jet ejector.

The hydrogen rejection step to produce methane or ethane normally employs a $H_2$:$CO_2$ molar ratio close to the stoichiometric proportions required for the desired Reaction 6 or Reaction 7, although small variations can be made in the stoichiometric ratio if it is desired to produce a $CO_2$-containing or $H_2$-containing second effluent stream. The hydrogen rejection step to produce methane or ethane is conveniently effected in the presence of a bifunctional catalyst comprising a metal component, particularly a transition metal or compound thereof, on an inorganic support. Suitable metal components comprise copper, iron, vanadium, chromium, zinc, gallium, nickel, cobalt, molybdenum, ruthenium, rhodium, palladium, silver, rhenium, tungsten, iridium, platinum, gold, gallium and combinations and compounds thereof. The inorganic support may be an amorphous material, such as silica, alumina or silica-alumina, or like those listed for the dehydroaromatization catalyst. In addition, the inorganic support may be a crystalline material, such as a microporous or mesoporous crystalline material. Suitable porous crystalline materials include the aluminosilicates, aluminophosphates and silicoaluminophosphates listed above for the dehydrocyclization catalyst.

The hydrogen rejection step to produce methane and/or ethane can be conducted over a wide range of conditions including a temperature of about 100° C. to about 900° C., such as about 150° C. to about 500° C., for example about 200° C. to about 400° C., a pressure of about 200 kPa to about 20,000 kPa, such as about 500 to about 5000 kPa and a weight hourly space velocity of about 0.1 to about 10,000 hr$^{-1}$, such as about 1 to about 1,000 hr$^{-1}$. $CO_2$ conversion levels are typically between 20 and 100% and preferably greater than 90%, such as greater than 99%. This exothermic reaction may be carried out in multiple catalyst beds with heat removal between beds. In addition, the lead bed(s) may be operated at higher temperatures to maximize kinetic rates and the tail beds(s) may be operated at lower temperatures to maximize thermodynamic conversion.

The main products of the reaction are water and, depending on the $H_2$:$CO_2$ molar ratio, methane, ethane and higher alkanes, together with some unsaturated $C_2$ and higher hydrocarbons. In addition, some partial hydrogenation of the carbon dioxide to carbon monoxide is preferred. After removal of the water, the methane, carbon monoxide, any unreacted carbon dioxide and higher hydrocarbons can be fed directly to the dehydrocyclization step to generate additional aromatic products.

Fischer-Tropsch Process

In another embodiment the hydrogen rejection step comprises reaction of at least part of the hydrogen in the dehydrocyclization effluent with carbon monoxide according to the Fischer-Tropsch process to produce $C_2$ to $C_5$ paraffins and olefins.

The Fischer-Tropsch process is well known in the art, see for example, U.S. Pat. Nos. 5,348,982 and 5,545,674 incorporated herein by reference. The process typically involves the reaction of hydrogen and carbon monoxide in a molar ratio of about 0.5:1 to about 4:1, preferably about 1.5:1 to about 2.5:1, at a temperature of about 175° C. to about 400° C., preferably about 180° C. to about 240° C. and a pressure of about 1 to about 100 bar (100 to 10,000 kPa), preferably about 10 to about 40 bar (1,000 to 4,000 kPa), in the presence of a Fischer-Tropsch catalyst, generally a supported or unsupported Group VIII, non-noble metal, e.g., Fe, Ni, Run, Co, with or without a promoter, e.g. ruthenium, rhenium, hafnium, zirconium, titanium. Supports, when used, can be refractory metal oxides such as Group IVB, i.e., titania, zirconia, or silica, alumina, or silica-alumina. In one embodiment, the catalyst comprises a non-shifting catalyst, e.g., cobalt or ruthenium, preferably cobalt, with rhenium or zirconium as a promoter, preferably cobalt and rhenium supported on silica or titania, preferably titania.

In another embodiment, the hydrocarbon synthesis catalyst comprises a metal, such as Cu, Cu/Zn or Cr/Zn, on the ZSM-5 and the process is operated to generate significant quantities of single-ring aromatic hydrocarbons. An example of such a process is described in *Study of Physical Mixtures of $Cr_2O_3$-ZnO and ZSM-5 Catalysts for the Transformation of Syngas into Liquid Hydrocarbons* by Jose Erena; Ind. Eng. Chem Res. 1998, 37, 1211-1219, incorporated herein by reference.

The Fischer-Tropsch liquids, i.e., $C_5$+, are recovered and light gases, e.g., unreacted hydrogen and CO, $C_1$ to $C_3$ or $C_4$ and water are separated from the heavier hydrocarbons. The heavier hydrocarbons can then be recovered as products or fed to the dehydrocyclization step to generate additional aromatic products.

The carbon monoxide required for the Fischer-Tropsch reaction can be provided wholly or partly by the carbon monoxide present in or cofed with the methane-containing feed and generated as a by-product in the dehydrocyclization step. If required, additional carbon monoxide can be generated by feeding carbon dioxide contained, for example, in natural gas, to a shift catalyst whereby carbon monoxide is produced by the reverse water gas shift reaction:

$$CO_2 + H_2 \leftrightarrows CO + H_2O \quad \text{(Reaction 8)}$$

and by the following reaction:

$$CH_4 + H_2O \leftrightarrows CO + 3H_2$$

Alcohol Synthesis

In a further embodiment the hydrogen rejection step comprises reaction of at least part of the hydrogen in the dehydrocyclization effluent with carbon monoxide to produce $C_1$ to $C_3$ alcohols, and particularly methanol. The production of methanol and other oxygenates from synthesis gas is also well-known and is described in, for example, in U.S. Pat. Nos. 6,114,279; 6,054,497; 5,767,039; 5,045,520; 5,254,520; 5,610,202; 4,666,945; 4,455,394; 4,565,803; 5,385,949, the descriptions of which are incorporated herein by reference. Typically, the synthesis gas employed has a molar ratio of hydrogen ($H_2$) to carbon oxides ($CO + CO_2$) in the range of from about 0.5:1 to about 20:1, preferably in the range of from about 2:1 to about 10:1, with carbon dioxide optionally being present in an amount of not greater than 50% by weight, based on total weight of the syngas.

The catalyst used in the methanol synthesis process generally includes an oxide of at least one element selected from the group consisting of copper, silver, zinc, boron, magnesium, aluminum, vanadium, chromium, manganese, gallium, palladium, osmium and zirconium. Conveniently, the catalyst is a copper based catalyst, such as in the form of copper oxide, optionally in the presence of an oxide of at least one element selected from silver, zinc, boron, magnesium, aluminum, vanadium, chromium, manganese, gallium, palladium, osmium and zirconium. Conveniently, the catalyst contains copper oxide and an oxide of at least one element selected from zinc, magnesium, aluminum, chromium, and zirconium. In one embodiment, the methanol synthesis catalyst is selected from the group consisting of: copper oxides, zinc oxides and aluminum oxides. More preferably, the catalyst contains oxides of copper and zinc.

The methanol synthesis process can be conducted over a wide range of temperatures and pressures. Suitable temperatures are in the range of from about 150° C. to about 450° C., such as from about 175° C. to about 350° C., for example from about 200° C. to about 300° C. Suitable pressures are in the range of from about 1,500 kPa to about 12,500 kPa, such as from about 2,000 kPa to about 10,000 kPa, for example 2,500 kPa to about 7,500 kPa. Gas hourly space velocities vary depending upon the type of process that is used, but generally the gas hourly space velocity of flow of gas through the catalyst bed is in the range of from about 50 hr$^{-1}$ to about 50,000 hr$^{-1}$, such as from about 250 hr$^{-1}$ to about 25,000 hr$^{-1}$, more preferably from about 500 hr$^{-1}$ to about 10,000 hr$^{-1}$. This exothermic reaction may be carried out in either fixed or fluidized beds, including multiple catalyst beds with heat removal between beds. In addition, the lead bed(s) may be operated at higher temperatures to maximize kinetic rates and the tail beds(s) may be operated at lower temperatures to maximize thermodynamic conversion.

The resultant methanol and/or other oxygenates can be used in the alkylation step described below to convert the benzene generated in the dehydrocyclization step to xylenes, or can be used as a feedstock for the production of lower olefins, particularly ethylene and propylene. The conversion of methanol to olefins is a well-known process and is, for example, described in U.S. Pat. No. 4,499,327, incorporated herein by reference.

Alkylation

In one embodiment of the present process, at least part of the benzene produced in the dehydrocyclization step is subjected to an alkylation step to convert the benzene directly or indirectly to one or more xylenes. Alkylation of benzene is well known in the art and typically involves reaction of an olefin, alcohol or alkyl halide with the benzene in the gas or liquid phase in the presence of an acid catalyst. Suitable acid catalysts include medium pore zeolites (i.e., those having a Constraint Index of 2-12 as defined in U.S. Pat. No. 4,016, 218), including materials having the framework types MFI (e.g., ZSM-5 and silicalite), MEL (e.g., ZSM-11), MTW (e.g., ZSM-12), TON (e.g., ZSM-22), MTT (e.g., ZSM-23), MFS (e.g., ZSM-57) and FER (e.g., ZSM-35) and ZSM-48, as well as large pore zeolites (i.e. those having a Constraint Index of less than 2) such as materials having the framework types BEA (e.g., zeolite beta), FAU (e.g., ZSM-3, ZSM-20, zeolites X, Y, ultrastabilized Y and dealuminized Y), MOR (e.g., mordenite), MAZ (e.g., ZSM-4), MEI (e.g., ZSM-18) and MWW (e.g., MCM-22, PSH-3, SSZ-25, ERB-1, ITQ-1, ITQ-2, MCM-36, MCM-49 and MCM-56).

In one embodiment of the present process, benzene is recovered from the dehydrocyclization effluent and then alkylated with an olefin, such as ethylene produced as a by-product of a hydrogen rejection step employing ethanation/methanation. Typical conditions for carrying out the vapor phase alkylation of benzene with ethylene include a temperature of from about 650 to 900° F. (343 to 482° C.), a pressure of about atmospheric to about 3000 psig (100 to 20,800 kPa), a WHSV based on ethylene of from about 0.5 to about 2.0 hr$^{-1}$ and a mole ratio of benzene to ethylene of from 1:1 to 30:1. Liquid phase alkylation of benzene with ethylene may be carried out at a temperature between 300 and 650° F. (150 to 340° C.), a pressure up to about 3000 psig (20,800 kPa), a WHSV based on ethylene of from about 0.1 to about 20 hr$^{-1}$ and a mole ratio of benzene to ethylene of from 1:1 to 30:1.

Preferably, the benzene ethylation is conducted under at least partial liquid phase conditions using a catalyst comprising at least one of zeolite beta, zeolite Y, MCM-22, PSH-3, SSZ-25, ERB-1, ITQ-1, ITQ-2, ITQ-13, ZSM-5 MCM-36, MCM-49 and MCM-56.

The benzene ethylation can be conducted at the site of the dehydrocyclization/hydrogen rejection process or the benzene can be shipped to another location for conversion to ethylbenzene. The resultant ethylbenzene can then be isomerized by methods well known in the art to mixed xylenes.

In another embodiment of the present process, the alkylating agent is methanol or dimethylether (DME) and the alkylation step is conveniently effected in presence of catalyst comprising a zeolite, such as ZSM-5, zeolite beta, ITQ-13, MCM-22, MCM-49, ZSM-11, ZSM-12, ZSM-22, ZSM-23, ZSM-35, and ZSM-48, which has been modified by steaming so as to have a Diffusion Parameter for 2,2 dimethylbutane of about 0.1-15 sec$^{-1}$ when measured at a temperature of 120° C. and a 2,2 dimethylbutane pressure of 60 torr (8 kPa). Such a process is selective to the production of para-xylene and is described in, for example, U.S. Pat. No. 6,504,272, incorporated herein by reference.

Where methanol or DME is used as an alkylating agent in the process of the invention, it can be provided as a separate feed to the process or can at least partly be generated in situ by adding a carbon dioxide-containing feed gas, such as a natural gas stream, to part or all of the effluent from the dehydrocyclization step. In particular, the dehydrocyclization effluent, prior to any separation of the aromatic components, can be fed to a reverse shift reactor and reacted with the carbon dioxide-containing feed under conditions to increase the carbon monoxide content of the effluent by reactions, such as Reactions 5 and 8 above.

In addition, methane and $CO_2$ and/or steam may be fed to a reverse shift reactor to generate syngas which can then be mixed with a portion of the dehydrocyclization effluent to adjust the $H_2/CO/CO_2$ ratios as required for the alkylation step.

Typically, the reverse shift reactor contains a catalyst comprising a transition metal on a support, such as Fe, Ni, Cr, Zn on alumina, silica or titania, and is operated under conditions including a temperature of about 500° C. to about 1200° C., such as about 600° C. to about 1000° C., for example about 700° C. to about 950° C. and a pressure of about 1 kPa to about 10,000 kPa, such as about 2,000 kPa to about 10,000 kPa, for example about 3000 kPa to about 5,000 kPa. Gas hourly space velocities may vary depending upon the type of process used, but generally the gas hourly space velocity of flow of gas through the catalyst bed is in the range of about 50 $hr^{-1}$ to about 50,000 $hr^{-1}$, such as about 250 $hr^{-1}$ to about 25,000 $hr^{-1}$, more preferably about 500 $hr^{-1}$ to about 10,000 $hr^{-1}$.

The effluent from the reverse shift reactor can then be fed to an alkylation reactor operating under conditions to cause reactions such as the following to occur:

$$CO + 2H_2 \leftrightarrows CH_3OH \quad \text{(Reaction 9)}$$

$$CH_3OH + C_6H_6 \rightarrow \text{toluene} + 2H_2O \quad \text{(Reaction 10)}$$

$$2CH_3OH + C_6H_6 \rightarrow \text{xylenes} + 2H_2O \quad \text{(Reaction 11)}$$

Suitable conditions for such an alkylation reactor would include a temperature of about 100 to about 700° C., a pressure of about 1 to about 300 atmospheres (100 to 30,000 kPa), and a WHSV for the aromatic hydrocarbon of about 0.01 to about 100 $hr^{-1}$. A suitable catalyst would comprise a molecular sieve having a constraint index of 1 to 12, such as ZSM-5, typically together with one or metals or metal oxides, such as copper, chromium and/or zinc oxide.

Preferably, where the alkylation catalyst includes a molecular sieve, the latter is modified to change its diffusion characteristics such that the predominant xylene isomer produced by Reaction 11 is paraxylene. Suitable means of diffusion modification include steaming and ex-situ or in-situ deposition of silicon compounds, coke, metal oxides, such as MgO, and/or P on the surface or in the pore mouths of the molecular sieve. Also preferred is that an active metal be incorporated into the molecular sieve so as to saturate more highly reactive species, such as olefins, which may be generated as by-products and which could otherwise cause catalyst deactivation.

The effluent from the alkylation reactor could then be fed to a separation section in which the aromatic products would initially be separated from the hydrogen and other low molecular weight materials, conveniently by solvent extraction. The aromatics products could then be fractionated into a benzene fraction, a toluene fraction, a $C_8$ fraction and a heavy fraction containing naphthalene and alkylated naphthalenes. The $C_8$ aromatic fraction could then be fed to a crystallization or sorption process to separate the valuable p-xylene component and the remaining mixed xylenes either sold as product or fed to an isomerization loop to generate more p-xylene. The toluene fraction could either be removed as saleable product, recycled to the alkylation reactor or fed to a toluene disproportionation unit, and preferably a selective toluene disproportionation unit for the preparation of additional p-xylene.

Further Processing

The benzene and xylene produced by the present process can either be recovered for sale as commodity chemicals or can be subjected to further processing to produce useful derivatives. Such derivatives include, for example, toluene, ethylbenzene, styrene, polystyrene, phenol, and polyethylene terephthalate, as well as derivatives in which the benzene ring is not retained, such as cyclohexane and nylon. It will be appreciated that, depending on the processes used to produce these derivatives, any benzene rings will retain the novel deuterium and $^{13}C$ isotope distribution of the benzene and xylene of the invention.

Isotope Distribution

The distribution of the isotopes deuterium and $^{13}C$ in a sample of benzene or xylene is conveniently defined in terms of the divergence from the natural abundance of deuterium in hydrogen, $\delta(\text{deuterium})$, and the divergence from the natural abundance of $^{13}C$ in $^{12}C$, $\delta(^{13}C)$, according to the equations:

$$\delta(\text{deuterium}) = (R'_{sample}/R'_{standard} - 1) \times 1000$$

where $R'_{sample}$ is the ratio of deuterium to hydrogen in the benzene or xylene; and $R'_{standard}$ is the ratio of the natural abundance of deuterium to the natural abundance of hydrogen (which is equal to 0.00015/0.99985); and $$\delta(^{13}C) = (R''_{sample}/R''_{standard} - 1) \times 1000$$

where $R''_{sample}$ is the ratio of $^{13}C$ to $^{12}C$ in the benzene or xylene; and $R''_{standard}$ is the ratio of the natural abundance of $^{13}C$ to the natural abundance of $^{12}C$ (which is equal to 0.01109/0.98891).

A spreadsheet model was developed to determine the isotopic composition of primary aromatic products and derivatives based on feed compositions. In all cases it was assumed that no isotopic partitioning occurred during reactions. All measurements referred to herein of the deuterium and $^{13}C$ contents of benzene and xylene are made using high resolution mass spectrometer techniques well know in the art The primary inputs are the isotopic compositions of the naturally geologically occurring species as listed in Table 1.

TABLE 1

| Component | $\delta(^{13}C)$ | | $\delta(\text{Deuterium})$ | |
| --- | --- | --- | --- | --- |
| | Low | High | Low | High |
| Geologic Methane | −60 | −36 | −450 | −250 |
| Geologic $CO_2$ | −15 | 5 | — | — |
| Naphtha | −32 | −13 | −250 | −100 |

Utilizing these compositional ranges and the spreadsheet model the isotopic compositions for benzene, and xylenes, produced by known processes were calculated and are shown in Table 2.

TABLE 2

| Component | δ($^{13}$C) Low | δ($^{13}$C) High | δ(Deuterium) Low | δ(Deuterium) High |
|---|---|---|---|---|
| Benzene from Naphtha | −32 | −13 | −250 | −100 |
| Benzene from Methane | −60 | −36 | −450 | −250 |
| Xylene from Naphtha | −32 | −13 | −250 | −100 |

Utilizing the same compositional ranges and the spreadsheet model the isotopic compositions were calculated for the primary products of the process of the invention and are shown in Table 3.

TABLE 3

| Component | δ($^{13}$C) Low | δ($^{13}$C) High | δ(Deuterium) Low | δ(Deuterium) High |
|---|---|---|---|---|
| Benzene | −59 | −24 | −450 | −250 |
| Xylene | −60 | −24 | −450 | −250 |
| Hydrogen | — | — | −450 | −250 |

Thus in Table 3 it is assumed that the benzene is produced by a process in which methane is dehydrocyclized to produce a first effluent stream comprising benzene and hydrogen, at least part of the hydrogen from the first effluent stream is reacted with CO and/or $CO_2$ to produce a second effluent stream having a reduced hydrogen content and an enhanced hydrocarbon content as compared with the first effluent stream, and at least part of the second effluent stream is recycled to the dehydrocyclization step. Benzene produced by such a process has a δ(deuterium) value of less than −250, such as less than −260, for example less than −270, such as less than −280, conveniently less than −290 or even less than −300 and has a δ($^{13}$C) value of greater than −59, such as greater than −57, for example greater than −55, such as greater than −53, conveniently greater than −51 or even greater than −49. More preferably, the benzene has a δ($^{13}$C) value of greater than −36, such as greater than −34, for example greater than −33, such as greater than −32, conveniently greater than −31 or even greater than −30. Typically, the benzene produced has a δ(deuterium) value of greater than −450, such as greater than −440, for example greater than −430, such as greater than −420, conveniently greater than −410 or even greater than −400 and has a δ($^{13}$C) value of less than −24, such as less than −25, for example less than −26, such as less than −27, conveniently less than −28 or even less than −29.

It is to be understood the entirety of ranges shown in Table 3 are included in the scope of this invention; that is the benzene having any combination of a δ($^{13}$C) value of about −59, −58, −57, −56, −55, −54, −53, −52, −51, −50, −49, −48, −47, −46, −45, −44, −42, −40, −38, −36, −34, −32, −30, −28, −26, or −24; and a δ(deuterium) value of about −450, −440, −430, −420, −410, −400, −390, −380, −370, −360, −350, −340, −330, −320, −310, −300, −290, −280, −270, −260, or −250.

Similarly in Table 3 it is assumed that the xylene is produced by a process in which methane is dehydrocyclized to produce a first effluent stream comprising benzene and hydrogen and at least part of the benzene from said first effluent stream is reacted with an alkylating agent to produce alkylbenzene. It is also assumed that at least part of the hydrogen from the first effluent stream can be reacted with CO and/or $CO_2$, to produce a second effluent stream having a reduced hydrogen content and an enhanced hydrocarbon content as compared with the first effluent stream, with at least part of the second effluent stream being recycled to the dehydrocyclization step. Alternately at least part of the hydrogen may be reacted with CO and/or $CO_2$ to produce methanol and the methanol be utilized as an alkylating agent to produce xylenes from benzene. Xylene produced by such a process has a δ(deuterium) value of less than −250, such as less than −260, for example less than −270, such as less than −280, conveniently less than −290 or even less than −300. In one embodiment, the xylene has a δ($^{13}$C) value of less than −24, such as less than −25, for example less than −26, such as less than −27, conveniently less than −28 or even less than −29. In another embodiment, the xylene has a δ($^{13}$C) value of less than −32, such as less than −34, for example less than −36, such as less than −38, conveniently less than −40 or even less than −42. Typically, the xylene produced has a δ(deuterium) value of greater than −450, such as greater than −440, for example greater than −430, such as greater than −420, conveniently greater than −410 or even greater than −400 and has a δ($^{13}$C) value of greater than −60, such as greater than −58, for example greater than −56, such as greater than −54, conveniently greater than −52 or even greater than −50.

It is to be understood the entirety of ranges shown in Table 3 are included in the scope of this invention; that is the xylene having any combination of a δ($^{13}$C) value of about −60, −59, −58, −57, −56, −55, −54, −53, −52, −51, −50, −49, −48, −47, −46, −45, −44, −42, −40, −38, −36, −34, −32, −30, −28, −26, or −24; and a δ(deuterium) value of about −450, −440, −430, −420, −410, −400, −390, −380, −370, −360, −350, −340, −330, −320, −310, −300, −290, −280, −270, −260, or −250.

It is also recognized that naphthalene may be co-produced with benzene and will have equivalent isotopic compositional shifts, δ(deuterium) and δ($^{13}$C) values, as the benzene.

Utilizing the same compositional ranges and the spreadsheet model the isotopic compositions were calculated for various derivatives of the benzene and xylene produced according to the invention. The results are shown in Table 4.

TABLE 4

| Component | δ($^{13}$C) Low | δ($^{13}$C) High | δ(Deuterium) Low | δ(Deuterium) High |
|---|---|---|---|---|
| Ethylbenzene | −60 | −22 | −450 | −213 |
| Cumene | −60 | −21 | −450 | −175 |
| Styrene | −60 | −22 | −450 | −213 |
| Polystyrene | −60 | −22 | −450 | −213 |
| Polyethylene Terephthalate | −57 | −22 | −400 | −175 |
| Phenol | −59 | −24 | −433 | −225 |
| Cyclohexane | −59 | −24 | −450 | −175 |
| Nylon6,6 | −52 | −19 | −400 | −138 |
| Toluene | −59 | −24 | −450 | −250 |

It is to be understood the entirety of ranges shown in Table 4 are included in the scope of this invention that is the polystyrene having any combination of a δ($^{13}$C) value of about −60, −59, −58, −57, −56, −55, −54, −53, −52, −51, −50, −49, −48, −47, −46, −45, −44, −42, −40, −38, −36, −34, −32, −30, −28, −26, −24, or −22; and a δ(deuterium) value of about −450, −440, −430, −420, −410, −400, −390, −380, −370, −360, −350, −340, −330, −320, −310, −300, −290, −280, −270, −260, −250, −240, −230, −220, or −213.

It is to be understood the entirety of ranges shown in Table 4 are included in the scope of this invention that is the polyethylene terephthalate having any combination of a $\delta(^{13}C)$ value of about −52, −51, −50, −49, −48, −47, −46, −45, −44, −42, −40, −38, −36, −34, −32, −30, −28, −26, −24, −22, −20, or, −19; and a $\delta(deuterium)$ value of about −400, −390, −380, −370, −360, −350, −340, −330, −320, −310, −300, −290, −280, −270, −260, −250, −240, −230, −220, or −210, −200, −190, −180, or −175.

It is to be understood the entirety of ranges shown in Table 4 are included in the scope of this invention that is the nylon having any combination of a $\delta(^{13}C)$ value of about −57, −56, −55, −54, −53, −52, −51, −50, −49, −48, −47, −46, −45, −44, −42, −40, −38, −36, −34, −32, −30, −28, −26, −24, or −22; and a $\delta(deuterium)$ value of about −400, −390, −380, −370, −360, −350, −340, −330, −320, −310, −300, −290, −280, −270, −260, −250, −240, −230, −220, or −210, −200, −190, −180, −170, −160, −150, −140, or −138.

In another embodiment, the measured isotope distribution of an aromatic hydrocarbon may be used to identify the type of manufacturing process that was used in its production. Thus, for example, a sample of benzene of unknown origin with a measured $\delta(deuterium)$ value of less than −250 and a $\delta(^{13}C)$ value of less than −32 could be uniquely identified as originating from a methane dehydrocyclization process as opposed to a naphtha reforming process. This novel ability to identify the production process of an aromatic hydrocarbon is based on the realization that the amounts of deuterium and $^{13}C$ present in an aromatic hydrocarbon product can serve to differentiate between an aromatic hydrocarbon produced from naphtha, the same aromatic hydrocarbon produced by dehydrocyclization of naturally-occurring geologic methane alone and the same aromatic hydrocarbon produced by dehydrocyclization of naturally-occurring geologic methane and methane produced from $CO_2$.

While an attempt has been made herein to disclose all embodiments and applications of the disclosed subject matter that could be reasonably foreseen. However, there may be unforeseeable, insubstantial modifications which remain as equivalents. Moreover, while the present disclosure has been described in conjunction with specific, exemplary embodiments thereof, it is evident that many alterations, modifications, combinations, and variations will be apparent to those skilled in the art in light of the foregoing description without departing from the spirit or scope of the present disclosure. Accordingly, the present disclosure is intended to embrace all such alterations, modifications, combinations and variations of the above detailed description and examples.

I claim:

1. Benzene comprising deuterium and $^{13}C$ in amounts in amounts such that $\delta(deuterium)$ for the benzene is less than −250 and $\delta(^{13}C)$ for the benzene is greater than −36, wherein $\delta(deuterium)$ and $\delta(^{13}C)$ are as defined as follows:

$$\delta(deuterium)=(R'_{sample}/R'_{standard}-1)\times 1000$$

where $R'_{sample}$ is the ratio of deuterium to hydrogen in the benzene; and
$R'_{standard}$ is the ratio of the natural abundance of deuterium to the natural abundance of hydrogen; and $$\delta(^{13}C)=(R''_{sample}/R''_{standard}-1)\times 1000$$

where $R''_{sample}$ is the ratio of $^{13}C$ to $^{12}C$ in the benzene; and
$R''_{standard}$ is the ratio of the natural abundance of $^{13}C$ to the natural abundance of $^{12}C$.

2. Benzene as claimed in claim 1 wherein the $\delta(deuterium)$ value for the benzene is greater than −450 and less than −250.

3. Benzene as claimed in claim 1 wherein the $\delta(^{13}C)$ value for the benzene is greater than −36 and less than −24.

4. Benzene comprising deuterium and $^{13}C$ in amounts such that $\delta(deuterium)$ for the benzene is less than −250 or $\delta(^{13}C)$ for the benzene is less than −24, wherein $\delta(deuterium)$ and $\delta(^{13}C)$ are as defined in claim 1, the benzene being produced by a process comprising:
    (a) contacting a feed containing methane with a dehydrocyclization catalyst under conditions effective to convert the methane to aromatic hydrocarbons including benzene and produce a first effluent stream comprising aromatic hydrocarbons and hydrogen, wherein the first effluent stream comprises at least 5 wt % more aromatic rings than said feed;
    (b) reacting at least part of the hydrogen from the first effluent stream with CO and/or $CO_2$, to produce a second effluent stream having a reduced hydrogen content and an enhanced hydrocarbon content as compared with the first effluent stream; and
    (c) recycling at least part of the second effluent stream to said contacting (a).

5. Benzene as claimed in claim 4 wherein the methane is produced from natural gas.

6. Benzene as claimed in claim 4 wherein the methane and the CO and/or $CO_2$ are produced from natural gas.

7. Benzene as claimed in claim 4 wherein the methane and the CO and/or $CO_2$ are produced from the same natural gas stream.

8. Benzene as claimed in claim 4 wherein the $\delta(deuterium)$ value for the benzene is greater than −450 and less than −250.

9. Benzene as claimed in claim 4 wherein the $\delta(^{13}C)$ value for the benzene is greater than −59 and less than −24.

10. Naphthalene co-produced with the benzene of claim 4 and having a $\delta(deuterium)$ value of less than −250 or a $\delta(^{13}C)$ value of less than −24.

11. Xylene comprising deuterium and $^{13}C$ in amounts such that the $\delta(deuterium)$ value for the xylene is less than −250 and the $\delta(^{13}C)$ value for the xylene is less than −24, wherein $\delta(deuterium)$ and $\delta(^{13}C)$ are as defined as follows:

$$\delta(deuterium)=(R'_{sample}/R'_{standard}-1)\times 1000$$

where $R'_{sample}$ is the ratio of deuterium to hydrogen in the xylene; and
$R'_{standard}$ is the ratio of the natural abundance of deuterium to the natural abundance of hydrogen; and $$\delta(^{13}C)=(R''_{sample}/R''_{standard}-1)\times 1000$$

where $R''_{sample}$ is the ratio of $^{13}C$ to $^{12}C$ in the xylene; and
$R''_{standard}$ is the ratio of the natural abundance of $^{13}C$ to the natural abundance of $^{12}C$.

12. Xylene as claimed in claim 11 wherein the $\delta(deuterium)$ value for the xylene is greater than −450 and less than −250.

13. Xylene as claimed in claim 11 wherein the $\delta(^{13}C)$ value for the xylene is greater than −60 and less than −24.

14. Xylene comprising deuterium and $^{13}C$ in amounts such that the $\delta(deuterium)$ value for the xylene is less than −250 or the $\delta(^{13}C)$ value for the xylene is less than −32, wherein $\delta(deuterium)$ and $\delta(^{13}C)$ are as defined in claim 11.

15. Xylene as claimed in claim 14 wherein the $\delta(^{13}C)$ value for the xylene is greater than −60 and less than −32.

16. Xylene comprising deuterium and $^{13}C$ in amounts such that the $\delta(deuterium)$ value is less than −250 or the $\delta(^{13}C)$ value is less than −24, wherein $\delta(deuterium)$ and $\delta(^{13}C)$ are as defined in claim 11, the xylene being produced by a process comprising:
    (a) contacting a feed containing methane with a dehydrocyclization catalyst under conditions effective to convert the methane to aromatic hydrocarbons including benzene and produce a first effluent stream comprising aromatic hydrocarbons and hydrogen; and (b) contacting at least a portion of the benzene from said first effluent stream with an alkylating agent under conditions effective to alkylate said benzene and produce alkylbenzene.

17. Xylene as claimed in claim 16 wherein the δ(deuterium) value for the xylene is greater than −450 and less than −250.

18. Xylene as claimed in claim 16 wherein the δ($^{13}$C) value for the xylene is greater than −60 and less than −24.

19. Xylene as claimed in claim 16 wherein the methane is produced from natural gas.

20. Xylene as claimed in claim 16 wherein the alkylating agent comprises or is produced from hydrogen and CO and/or $CO_2$.

21. Xylene as claimed in claim 20 wherein the methane and the CO and/or $CO_2$ are produced from natural gas.

22. Xylene as claimed in claim 20 wherein the methane the CO and/or $CO_2$ are produced from the same natural gas stream.

23. Xylene comprising deuterium and $^{13}$C in amounts such that the δ(deuterium) value is less than −250 or the δ($^{13}$C) value is less than −24, wherein δ(deuterium) and δ($^{13}$C) are as defined in claim 11, the xylene being produced by a process comprising:

(a) contacting a feed containing methane with a dehydrocyclization catalyst under conditions effective to convert the methane to aromatic hydrocarbons including benzene and produce a first effluent stream comprising aromatic hydrocarbons and hydrogen;

(b) reacting at least part of the hydrogen from the first effluent stream with CO and/or $CO_2$, to produce a second effluent stream having a reduced hydrogen content and an enhanced hydrocarbon content as compared with the first effluent stream;

(c) recycling at least part of the second effluent stream to said contacting (a); and (d) contacting at least a portion of the benzene from said first effluent stream with an alkylating agent under conditions effective to alkylate said benzene and produce alkylbenzene.

24. Xylene as claimed in claim 23 wherein the δ(deuterium) value for the xylene is greater than −450 and less than −250.

25. Xylene as claimed in claim 23 wherein the δ($^{13}$C) value for the xylene is greater than −60 and less than −24.

26. Xylene as claimed in claim 23 wherein the methane is produced from natural gas.

27. Xylene as claimed in claim 23 wherein the methane and the CO and/or $CO_2$ are produced from natural gas.

28. Xylene as claimed in claim 23 wherein the methane the CO and/or $CO_2$ are produced from the same natural gas stream.

29. A hydrocarbon product produced from the benzene of claim 1 and selected from toluene, cumene, ethylbenzene, styrene, polystyrene, phenol, polyethylene terephthalate, cyclohexane, and nylon.

30. A hydrocarbon product produced from the benzene of claim 4 and selected from toluene, cumene, ethylbenzene, styrene, polystyrene, phenol, polyethylene terephthalate, cyclohexane, and nylon.

31. A hydrocarbon product produced from the xylene of claim 11 and selected from toluene, cumene, ethylbenzene, styrene, polystyrene, phenol, polyethylene terephthalate, cyclohexane, and nylon.

32. A hydrocarbon product produced from the xylene of claim 14 and selected from toluene, cumene, ethylbenzene, styrene, polystyrene, phenol, polyethylene terephthalate, cyclohexane, and nylon.

33. A hydrocarbon product produced from the xylene of claim 16 and selected from toluene, cumene, ethylbenzene, styrene, polystyrene, phenol, polyethylene terephthalate, cyclohexane, and nylon.

34. A hydrocarbon product produced from the xylene of claim 23 and selected from toluene, cumene, ethylbenzene, styrene, polystyrene, phenol, polyethylene terephthalate, cyclohexane, and nylon.

35. A hydrocarbon product selected from toluene, cumene, ethylbenzene, styrene, polystyrene, phenol, polyethylene terephthalate, cyclohexane, and nylon and having δ(deuterium) and δ($^{13}$C) values within the ranges listed in Table 4.

36. The hydrocarbon product of claim 29, wherein said hydrocarbon product comprises toluene.

37. The hydrocarbon product of claim 29, wherein said hydrocarbon product comprises cumene.

38. The hydrocarbon product of claim 29, wherein said hydrocarbon product comprises ethylbenzene.

39. The hydrocarbon product of claim 29, wherein said hydrocarbon product comprises styrene.

40. The hydrocarbon product of claim 29, wherein said hydrocarbon product comprises polystyrene.

41. The hydrocarbon product of claim 29, wherein said hydrocarbon product comprises phenol.

42. The hydrocarbon product of claim 29, wherein said hydrocarbon product comprises polyethylene terephthalate.

43. The hydrocarbon product of claim 29, wherein said hydrocarbon product comprises cyclohexane.

44. The hydrocarbon product of claim 29, wherein said hydrocarbon product comprises nylon.

45. The hydrocarbon product of claim 30, wherein said hydrocarbon product comprises toluene.

46. The hydrocarbon product of claim 30, wherein said hydrocarbon product comprises cumene.

47. The hydrocarbon product of claim 30, wherein said hydrocarbon product comprises ethylene.

48. The hydrocarbon product of claim 30, wherein said hydrocarbon product comprises styrene.

49. The hydrocarbon product of claim 30 wherein said hydrocarbon product comprises polystyrene.

50. The hydrocarbon product of claim 30, wherein said hydrocarbon product comprises phenol.

51. The hydrocarbon product of claim 30, wherein said hydrocarbon product comprises polyethylene terephthalate.

52. The hydrocarbon product of claim 30, wherein said hydrocarbon product comprises cyclohexane.

53. The hydrocarbon product of claim 30, wherein said hydrocarbon product comprises nylon.

54. In an aromatic hydrocarbon product selected from benzene and derivatives therefrom selected from the group consisting of cumene, xylene, ethylbenzene, styrene, polystyrene, phenol, polyethylene terephthalate, cyclohexane, and nylon, the improvement comprising said product containing a benzene ring comprising deuterium and $^{13}$C in amounts in amounts such that δ(deuterium) for the benzene is less than −250 and δ($^{13}$C) for the benzene is less than −24, wherein δ(deuterium) and δ($^{13}$C) are as defined as follows:

$$\delta(\text{deuterium}) = (R'_{sample}/R'_{standard} - 1) \times 1000$$

where $R'_{sample}$ is the ratio of deuterium to hydrogen in the benzene; and $R'_{standard}$ is the ratio of the natural abundance of deuterium to the natural abundance of hydrogen; and $$\delta(^{13}C) = (R''_{sample}/R''_{standard} - 1) \times 1000$$

where $R''_{sample}$ is the ratio of $^{13}C$ to $^{12}C$ in the benzene; and $R''_{standard}$ is the ratio of the natural abundance of $^{13}C$ to the natural abundance of $^{12}C$, made by a process incorporating geologic methane in said benzene ring, whereby said product can be distinguished by mass spectrometry analysis.

55. The product of claim 54, wherein the δ(deuterium) value for said benzene ring is greater than −450 and less than −250, and wherein the $\delta(^{13}C)$ value for said benzene ring is greater than −36 and less than −24.

56. The product of claim 54, wherein said process incorporates geologic $CO_2$ and/or geologic CO in said benzene ring.

57. The product of claim 54, wherein said process incorporates geologic methane and geologic $CO_2$ and/or geologic CO in said benzene ring, whereby said product can be distinguished from a benzene ring not incorporating said geologic methane and geologic $CO_2$ and/or geologic CO.

58. The product of claim 54, wherein said product is nylon.

59. The product of claim 57, wherein said product is nylon.

* * * * *